United States Patent
Banowski et al.

(10) Patent No.: US 9,408,787 B2
(45) Date of Patent: *Aug. 9, 2016

(54) COSMETIC AEROSOL SPRAY

(71) Applicant: Henkel AG & Co. KGaA, Duesseldorf (DE)

(72) Inventors: Bernhard Banowski, Duesseldorf (DE); Nadine Schneider, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 154 days.

This patent is subject to a terminal disclaimer.

(21) Appl. No.: 13/772,913

(22) Filed: Feb. 21, 2013

(65) Prior Publication Data

US 2013/0164238 A1   Jun. 27, 2013

Related U.S. Application Data

(63) Continuation of application No. PCT/EP2011/065043, filed on Aug. 31, 2011.

(30) Foreign Application Priority Data

Sep. 1, 2010   (DE) .......................... 10 2010 040 121

(51) Int. Cl.
| | | |
|---|---|---|
| *A61K 8/04* | (2006.01) | |
| *A61Q 15/00* | (2006.01) | |
| *A61K 8/894* | (2006.01) | |
| *A61K 8/06* | (2006.01) | |
| *A61K 8/31* | (2006.01) | |
| *A61K 8/26* | (2006.01) | |
| *A61K 8/86* | (2006.01) | |

(52) U.S. Cl.
CPC .................. *A61K 8/046* (2013.01); *A61K 8/064* (2013.01); *A61K 8/26* (2013.01); *A61K 8/31* (2013.01); *A61K 8/86* (2013.01); *A61K 8/894* (2013.01); *A61Q 15/00* (2013.01)

(58) Field of Classification Search
CPC ......... A61K 8/06; A61K 8/894; A61K 8/064; A61K 8/31; A61K 8/26; A61K 8/86; A61Q 15/00

See application file for complete search history.

(56) References Cited

U.S. PATENT DOCUMENTS

| | | | |
|---|---|---|---|
| 2007/0190004 A1* | 8/2007 | Bockmuhl | A61K 8/33 424/65 |
| 2011/0250160 A1 | 10/2011 | Banowski et al. | |
| 2013/0280175 A1 | 10/2013 | Banowski et al. | |

FOREIGN PATENT DOCUMENTS

| | | |
|---|---|---|
| DE | 102005024595 A1 | 11/2006 |
| DE | 102006062499 A1 | 7/2008 |
| WO | 2012/084972 A1 | 6/2012 |

OTHER PUBLICATIONS

Emulsifiers with HLB values [retrieved on Dec. 4, 2014 from on-line website http://www.theherbarie.com/files/resource-center/formulating/Emulsifiers_HLB_Values.pdf].*

An English translation of DE 102005024595A1 (machine translated by Ecepacenet) [retrieved on Dec. 4, 2014 from http://translationportal.epo.org/emtp/translate/?ACTION=description-retrieval&COUNTRY=DE&ENGINE=google&FORMAT=docdb &KIND=A1&LOCALE=en_EP&NUMBER=102005024595 &OPS=ops.epo.org/3.1&SRCLANG=de&TRGLANG=en].*

PCT International Search Report (PCT/EP2011/065043) dated Aug. 5, 2014.

* cited by examiner

*Primary Examiner* — Ernst V Arnold
*Assistant Examiner* — Kyung Sook Chang
(74) *Attorney, Agent, or Firm* — P. Scott Smith

(57) ABSTRACT

A cosmetic product includes a water-in-oil emulsion containing: a) at least one cosmetic active ingredient, b) at least one water-in-oil emulsifier, c) at least one non-ionic polyalkylene glycol ether having a HLB value >7, d) at least one $C_8$-$C_{16}$ isoparaffin, and also including at least one propellant and an aerosol dispensing device. The emulsion has a high stability, a reduced susceptibility to corrosion, a good cosmetic effect and reduced formation of deposits during the application thereof.

9 Claims, No Drawings

COSMETIC AEROSOL SPRAY

FIELD OF THE INVENTION

The present invention generally relates to cosmetic water-in-oil emulsions which can be sprayed as an aerosol. This application also provides a method using corresponding emulsions.

BACKGROUND OF THE INVENTION

An aerosol is a disperse system in which a solid or liquid is present in very finely divided form in a gas. The aerosol itself is generally produced only upon application using a suitable spray system by the spraying of solutions, emulsions or suspensions, for which purpose e.g. spray cans may be used in which a liquefied compressed gas acts as propellant. When the valve is opened, the propellant/preparation mixture is released through a fine nozzle, and the propellant evaporates leaving the finely divided spray product as an aerosol.

An important technical field for the application of cosmetic aerosol sprays is the field of deodorizing cosmetic products. Common deodorant spray compositions often take the form of anhydrous ethanolic solutions of the deodorizing active ingredient. One disadvantage of these ethanolic solutions is a skin-irritating effect in persons with a relevant predisposition having sensitive skin. Likewise on skin that has been mechanically irritated by shaving, application of the common ethanolic solutions leads to a very unpleasant burning sensation. A further disadvantage of ethanolic solutions is that the incorporation of aqueous or water-soluble active ingredients, in particular of antiperspirant or deodorant active ingredients or hair growth inhibiting active ingredients which are not also soluble in ethanol, can be achieved only to a limited degree or not at all.

As an alternative presentation to the ethanolic solutions, anhydrous suspensions of the powdered sweat-reducing active ingredient, usually an aluminum salt, in addition to the propellant in a liquid carrier, usually a relatively volatile oil such as cyclomethicone, are discussed in the prior art. Before spraying, the suspension must be shaken. One disadvantage of these suspension aerosols is the risk that the valve or nozzle apertures become blocked when relatively high concentrations of the salt are used. Attempts have therefore been made to spray the antiperspirant salt in dissolved form. However, the packaging of aqueous antiperspirant salt solutions in propellant-containing metal cans causes serious corrosion problems in aerosol packaging, so that even with lacquered spray cans, corrosion phenomena inevitably occur on the can.

As another alternative presentation, the prior art describes water-in-oil emulsions (W/O emulsions). For instance the German patent application DE 10 2006 062 499 A1 (Henkel) describes a W/O emulsion which is suitable as an aerosol spray. The emulsions disclosed in this application contain cyclomethicones, however. Cyclomethicones have excellent performance characteristics, particularly in terms of emulsion stability, and for this reason they are widely used in cosmetics and particularly in antiperspirants. However, with too high a proportion of volatile cyclomethicones, after drying, i.e. some time after application, antiperspirants form white residues on the skin, which do not adhere well to the skin and are perceived by the user as unpleasant, particularly if they are transferred to dark-colored clothing.

There is therefore a need for a stable water-in-oil emulsion suitable for use in an aerosol spray with a low cyclomethicone and ethanol content. The emulsion should, in addition, be distinguished by a low corrosion tendency when stored in a metallic spray can and by a good cosmetic, particularly antiperspirant, action and low residue formation upon application. Furthermore, the cosmetic active ingredient should be released particularly well from the W/O formulation.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A cosmetic product, encompassing a water-in-oil emulsion, containing at least one cosmetic active ingredient, at least one water-in-oil emulsifier, at least one non-ionic polyalkylene glycol ether with an HLB value >7, at least one $C_8$-$C_{16}$ isoparaffin, at least one propellant, and an aerosol dispensing device.

A method for the cosmetic treatment of skin and/or hair, wherein a water-in-oil emulsion, containing at least one cosmetic active ingredient, at least one water-in-oil emulsifier, at least one non-ionic polyalkylene glycol ether with an HLB value >7, and at least one $C_8$-$C_{16}$ isoparaffin is applied onto the skin and/or hair in the form of an aerosol.

A method for the cosmetic treatment of body odor, wherein a water-in-oil emulsion containing at least one antiperspirant active ingredient, at least one water-in-oil emulsifier, at least one non-ionic polyalkylene glycol ether with an HLB value >7, and at least one $C_8$-$C_{16}$ isoparaffin is applied onto the skin in the form of an aerosol.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present application firstly provides a cosmetic product, encompassing a water-in-oil emulsion, containing
 a) at least one cosmetic active ingredient,
 b) at least one water-in-oil emulsifier,
 c) at least one non-ionic polyalkylene glycol ether with an HLB value >7,
 d) at least one $C_8$-$C_{16}$ isoparaffin,
at least one propellant, and an aerosol dispensing device.

The water-in-oil emulsions according to the invention contain at least one cosmetic active ingredient. This cosmetic active ingredient is preferably selected from the group of the antiperspirant active ingredients, deodorant active ingredients, antibacterial active ingredients, skincare active ingredients, skin tanning active ingredients, skin lightening active ingredients, haircare active ingredients and sun protection active ingredients. In addition, active ingredients which reduce hair growth are preferred. The cosmetic active ingredient is preferably water-soluble.

In a first preferred embodiment the water-in-oil emulsions according to the invention contain at least one sweat-inhibiting active ingredient (antiperspirant active ingredient).

The present application preferably provides a cosmetic product, encompassing a water-in-oil emulsion, containing
 a) at least one antiperspirant active ingredient,
 b) at least one water-in-oil emulsifier,
 c) at least one non-ionic polyalkylene glycol ether with an HLB value >7,
 d) at least one $C_8$-$C_{16}$ isoparaffin,
and at least one propellant.

Unless otherwise specified, all quantitative data in this application relate to the weight of the propellant-free water-in-oil emulsion according to the invention.

Preferred antiperspirant active ingredients are selected from the water-soluble astringent inorganic and organic salts of aluminum and zinc or any mixtures of these salts. Aluminosilicates and zeolites are not included in the antiperspirant active ingredients according to the invention. The term water solubility according to the invention means a solubility of at least 5 wt. % at 20° C., i.e. quantities of at least 5 g of the antiperspirant active ingredient are soluble in 95 g of water at 20° C.

Particularly preferred antiperspirant active ingredients are selected from aluminum chlorohydrate, in particular aluminum chlorohydrate with the general formula $[Al_2(OH)_5Cl.1\text{-}6H_2O]_n$, preferably $[Al_2(OH)_5Cl.2\text{-}3H_2O]_n$, which may be present in non-activated or in activated (=depolymerized) form, and aluminum chlorohydrate with the general formula $[Al_2(OH)_4Cl_2.1\text{-}6H_2O]_n$, preferably $[Al_2(OH)_4Cl_2.2\text{-}3H_2O]_n$, which may be present in non-activated or in activated (=depolymerized) form.

Also preferred are aluminum sesquichlorohydrate, aluminum dichlorohydrate or aluminum chlorohydrex polyethylene glycol (PEG), aluminum glycol complexes, e.g. aluminum-propylene glycol complexes, aluminum sesquichlorohydrex PG or aluminum sesquichlorohydrex PEG, or aluminum dichlorohydrex PEG, aluminum hydroxide, also selected from potassium aluminum sulfate (KAl$(SO_4)_2.12H_2O$, alum), aluminum undecylenoyl collagen amino acid, sodium aluminum lactate+aluminum sulfate, sodium aluminum chlorohydroxylactate, aluminum bromohydrate, aluminum chloride, the complexes of zinc and sodium salts, the aluminum salts of lipoamino acids, aluminum sulfate, aluminum lactate, aluminum chlorohydroxyallantoinate, sodium-aluminum chlorohydroxylactate, zinc chloride, zinc sulfocarbolate and zinc sulfate.

Particularly preferred antiperspirant active ingredients according to the invention are selected from so-called "activated" aluminum salts, which are also known as antiperspirant active ingredients "with enhanced activity". Activated aluminum salts are generally produced by heat treatment of a relatively dilute solution of the salt (e.g. about 10 wt. % salt) in order to increase its HPLC peak 4 to peak 3 area ratio. The activated salt can then be dried, in particular spray-dried, to form a powder. As well as spray drying, for example roller drying is also suitable.

Activated aluminum salts typically have an HPLC peak 4 to peak 3 area ratio of at least 0.4, preferably at least 0.7, particularly preferably at least 0.9, it being possible for at least 70% of the aluminum to be allocated to these peaks. Preferred amino acids for stabilizing the antiperspirant salt are selected from glycine, alanine, leucine, isoleucine, β-alanine, valine, cysteine, serine, tryptophan, phenylalanine, methionine, β-amino-n-butanoic acid and γ-amino-n-butanoic acid and the salts thereof, each in the d form, the l form and the dl form; glycine is particularly preferred.

Preferred hydroxyalkanoic acids for stabilizing the antiperspirant salts are selected from glycolic acid and lactic acid.

Other preferred antiperspirant active ingredients are activated aluminum salts containing, based on their weight, 5-78 wt. % (USP) of an activated antiperspirant aluminum salt, an amino acid or hydroxyalkanoic acid in a sufficient quantity to provide an (amino acid or hydroxyalkanoic acid) to Al weight ratio of 2:1-1:20 and preferably 1:1 to 1:10, as well as a water-soluble strontium salt in a sufficient quantity to provide a Sr:Al weight ratio of 1:1-1:28 and preferably 1:2-1:25.

Particularly preferred solid antiperspirant activated salt compositions contain, based on their weight, 48-78 wt. % (USP), preferably 66-75 wt. %, of an activated aluminum salt and 1-16 wt. %, preferably 4-13 wt. %, of molecularly bound water, as well as sufficient water-soluble strontium salt that the Sr:Al weight ratio is 1:1-1:28, preferably 1:2-1:25, and sufficient amino acid so that the amino acid to Al weight ratio is 2:1-1:20, preferably 1:1-1:10.

Other particularly preferred solid antiperspirant activated salt compositions contain, based on their weight, 48-78 wt. % (USP), preferably 66-75 wt. %, of an activated aluminum salt and 1-16 wt. %, preferably 4-13 wt. %, of molecularly bound water as well as sufficient water-soluble strontium salt that the Sr:Al weight ratio is 1:1-1:28, preferably 1:2-1:25, and sufficient glycine that the glycine to Al weight ratio is 2:1-1:20, preferably 1:1-1:10.

Other particularly preferred solid antiperspirant activated salt compositions contain, based on their weight, 48-78 wt. % (USP), preferably 66-75 wt. %, of an activated aluminum salt and 1-16 wt. %, preferably 4-13 wt. %, of molecularly bound water, as well as sufficient water-soluble strontium salt that the Sr:Al weight ratio is 1:1-1:28, preferably 1:2-1:25, and sufficient hydroxyalkanoic acid that the hydroxyalkanoic acid to Al weight ratio is 2:1-1:20, preferably 1:1-1:10.

Other preferred activated aluminum salts are those of the general formula $Al_2(OH)_{6-a}X_a$, wherein X is Cl, Br, I or $NO_3$ and "a" is a value of 0.3 to 5, preferably of 0.8 to 2.5 and particularly preferably 1 to 2, so that the molar ratio of Al:X is 0.9:1 to 2.1:1. In these salts, there is generally some associatively bonded water of hydration, typically 1 to 6 moles of water per mole of salt. Particularly preferred is aluminum chlorohydrate (i.e. X is Cl in the above formula) and especially 5/6-basic aluminum chlorohydrate, wherein "a" is 1, so that the molar ratio of aluminum to chlorine is 1.9:1 to 2.1:1.

Particularly preferred water-in-oil emulsions according to the invention contain at least one antiperspirant active ingredient in a total quantity of 5 to 40 wt. %, preferably 10 to 30 wt. %, particularly preferably 15 to 25 wt. % and extraordinarily preferably 20 to 23 wt. %, based in each case on the total weight of the active substance (USP) which is free from water of crystallization in the propellant-free water-in-oil emulsion.

In a particularly preferred embodiment the water-in-oil emulsion contains an astringent aluminum salt, in particular aluminum chlorohydrate, particularly preferably aluminum chlorohydrate with an active substance (USP) which is free from water of crystallization of 72-88 wt. %, based on the raw material in its natural state. In another particularly preferred embodiment, the water-in-oil emulsion contains a non-activated astringent aluminum salt, in particular aluminum chlorohydrate, particularly preferably aluminum chlorohydrate with an active substance (USP) which is free from water of crystallization of 72-88 wt. %, based on the raw material in its natural state. Preferred non-activated aluminum chlorohydrates are e.g. Chlorhydrol® (Summit-Reheis), ACH 303 (Summit-Reheis), Locron® L (Clariant) or Aloxicoll® L (Giulini). A preferred activated aluminum chlorohydrate solution is e.g. Reach® 501 from Summit-Reheis.

The present application preferably provides a cosmetic product, encompassing
 a water-in-oil emulsion, containing
  a) 5-40 wt. %, based on the total weight of the active substance (USP) which is free from water of crystallization in the propellant-free water-in-oil emulsion, of an antiperspirant active ingredient from the group of the antiperspirant aluminum salts,
  b) at least one water-in-oil emulsifier, c) at least one non-ionic polyalkylene glycol ether with an HLB value >7,
d) at least one $C_8$-$C_{16}$ isoparaffin,
at least one propellant,
an aerosol dispensing device.

The water-in-oil emulsions according to the invention contain at least one water-in-oil emulsifier as a second essential component. A surface-active substance having an HLB value in the range of 1.5 to 6 under normal conditions is regarded as a water-in-oil emulsifier within the meaning of the present application. "Normal conditions" within the meaning of the present application are a temperature of 20° C. and a pressure of 1013.25 hPa. Melting point data also relate to a pressure of 1013.25 hPa.

Water-in-oil emulsions in which the proportion by weight of the water-in-oil emulsifier b), based on the total propellant-free water-in-oil emulsion, is 0.2-4.0 wt. %, preferably 0.3-3.0 wt. % and in particular 0.4-2.0 wt. %, are preferred according to the invention.

A particularly preferred group of water-in-oil emulsifiers according to the invention are the poly($C_2$-$C_3$)alkylene glycol-modified silicones which previously had the INCI name Dimethicone Copolyol and have the current INCI names PEG-x Dimethicone (with x=2-20, preferably 3-17, particularly preferably 11-12), Bis-PEG-y Dimethicone (with y=3-25, preferably 4-20), PEG/PPG a/b Dimethicone (wherein a and b independently of one another denote numbers from 2-30, preferably 3-30 and particularly preferably 12-24, in particular 14-20), Bis-PEG/PPG-c/d Dimethicone (wherein c and d independently of one another denote numbers from 10-25, preferably 14-20 and particularly preferably 14-16) and Bis-PEG/PPG-e/f PEG/PPG g/h Dimethicone (wherein e, f, g and h independently of one another denote numbers from 10-20, preferably 14-18 and particularly preferably 16).

Particularly preferred water-in-oil emulsions according to the invention are characterized in that the water-in-oil emulsifier b) is selected from the group of the alkoxylated silicone emulsifiers, preferably from the group of the ethoxylated and propoxylated silicone emulsifiers, wherein with particular preference a substance from the group of the PEG/PPG-n/m Dimethicones with n+m>11, in particular with n+m between 16 and 46, preferably with n+m between 26 and 46, is used as water-in-oil emulsifier b). It should be noted for the sake of clarity that these preferred water-in-oil emulsifiers b) from the group of the PEG/PPG-n/m Dimethicones with n+m>11, in particular with n+m between 16 and 46, preferably with n+m between 26 and 46, are alkylated only with methyl groups and—as implied by the names "Dimethicone Copolyol" and "PEG/PPG Dimethicone"—do not have any higher alkyl groups, e.g. ethyl, lauryl or cetyl, in the molecule.

Most particularly preferred is PEG/PPG-18/18 Dimethicone. The particularly preferred water-in-oil emulsifier PEG/PPG-18/18 Dimethicone is generally available commercially not as a pure substance but dispersed in a cosmetic oil. Preferred products according to the invention encompass a water-in-oil emulsion containing the water-in-oil emulsifier PEG/PPG-18/18 Dimethicone as a dispersion in dimethicone having a viscosity of 3-100 cSt, preferably 5-50 cSt, particularly preferably 10-20 cSt (at 25° C. in each case). A particularly preferred commercial product is Dow Corning ES-5227 DM from Dow Corning.

The proportion by weight of the water-in-oil emulsifier b) is, in total, based on the total propellant-free water-in-oil emulsion, preferably 0.2 to 4.0 wt. %, for preference 0.3 to 3.0 wt % and in particular 0.4 to 2.0 wt. %.

The present application preferably provides a cosmetic product, encompassing
a water-in-oil emulsion, containing
a) at least one antiperspirant active ingredient,
b) 0.2 to 4.0 wt. % water-in-oil emulsifier from the group of the PEG/PPG-n/m Dimethicones with n+m between 16 and 46, preferably with n+m between 26 and 46,
c) at least one non-ionic polyalkylene glycol ether with an HLB value >7,
d) at least one $C_8$-$C_{16}$ isoparaffin,
at least one propellant,
an aerosol dispensing device.

The water-in-oil emulsions according to the invention contain at least one non-ionic polyalkylene glycol ether with an HLB value >7 as a third essential component. For the desired stability of emulsions according to the invention and the active ingredient release of the antiperspirant active ingredient, an HLB value of more than 7 has proved advantageous. Preferred water-in-oil emulsions according to the invention are characterized in that the non-ionic polyalkylene glycol ether c) has an HLB value >9, preferably an HLB value >12 and in particular an HLB value >14. Particularly preferred non-ionic polyalkylene glycol ethers c) have an HLB value of >14 to 20, preferably of 15 to 18, particularly preferably of 15.5 to 17.

The HLB value is determined according to the invention by Griffin's method according to the formula:
HLB=20*($M_h$/M), wherein $M_h$ is the molar mass of the hydrophilic portion of a molecule and M is the molar mass of the whole molecule. A scale of 0 to 20 is thus obtained.

The polyalkylene glycol ether c) is preferably selected from the group of the alkoxylated $C_8$-$C_{24}$ alkanols having on average 10-100 moles alkylene oxide per mole, preferably from the group of the ethoxylated $C_{12}$-$C_{18}$ alkanols with on average 10-30 moles ethylene oxide per mole, with an ethoxylated $C_{14}$-$C_{18}$ alkanol having on average 20-30 moles ethylene oxide per mole being used with particular preference as non-ionic polyalkylene glycol ether c). A particularly preferred polyalkylene glycol ether is an isocetyl alcohol ethoxylated with 20 moles ethylene oxide (Isoceteth-20).

The proportion by weight of the non-ionic polyalkylene glycol ether c), based on the total propellant-free water-in-oil emulsion, is preferably 0.1 to 4.0 wt. %, for preference 0.2 to 2.0 wt. % and in particular 0.5 to 1.0 wt. %.

The present application preferably provides a cosmetic product, encompassing
a water-in-oil emulsion, containing
a) at least one antiperspirant active ingredient,
b) at least one water-in-oil emulsifier,
c) 0.1 to 4.0 wt. % of a non-ionic polyalkylene glycol ether with an HLB value >7 from the group of the alkoxylated $C_3$-$C_{24}$ alkanols having on average 10-100 moles alkylene oxide per mole,
d) at least one $C_8$-$C_{16}$ isoparaffin,
at least one propellant,
an aerosol dispensing device.

The water-in-oil emulsions according to the invention contain at least one $C_8$-$C_{16}$ isoparaffin as a fourth essential component. The terms "isoparaffin" and "isoalkane" are used synonymously within the meaning of the present application. Preferred water-in-oil emulsions according to the invention are characterized in that the isoparaffin d) is selected from isooctane, isononane, isodecane, isoundecane, isododecane, isotridecane, isotetradecane, isopentadecane and isohexadecane and mixtures thereof, with $C_{10}$-$C_{13}$ isoparaffin mixtures, in particular those having a vapor pressure at 20° C. of about 1-100 Pa, being preferred. Extraordinarily preferred are isoparaffins having a vapor pressure of <40 Pa and >8 Pa.

The proportion by weight of the isoparaffin c), based on the total propellant-free water-in-oil emulsion, is in total preferably 4.0 to 20 wt. %, preferably 5.0 to 12 wt. % and in particular 6.0 to 10 wt. %.

The present application preferably provides a cosmetic product encompassing a water-in-oil emulsion, containing
- a) at least one antiperspirant active ingredient,
- b) at least one water-in-oil emulsifier,
- c) at least one non-ionic polyalkylene glycol ether with an HLB value >7,
- d) 4.0 to 20 wt. % of a $C_{10}$-$C_{13}$ isoparaffin mixture, at least one propellant, and an aerosol dispensing device.

By means of the combination according to the invention of
- at least one water-in-oil emulsifier,
- at least one non-ionic polyalkylene glycol ether with an HLB value >7 and
- at least one $C_8$-$C_{16}$ isoparaffin it was possible to produce stable emulsions with advantageous active ingredient release of the antiperspirant active ingredient and low residue formation at the same time as a low corrosion tendency.

It was also possible to reduce the cyclomethicone content of water-in-oil emulsions according to the invention without impairing the product properties. Preferred compositions according to the invention therefore contain, based on the total propellant-free water-in-oil emulsion, less than 5.0 wt. % cyclomethicones, preferably less than 3.0 wt. % cyclomethicones and particularly preferably less than 1.0 wt. % cyclomethicones. Most particularly preferred compositions according to the invention are free from cyclomethicones. The present application preferably provides a cosmetic product, encompassing a water-in-oil emulsion, containing
- a) at least one antiperspirant active ingredient,
- b) at least one water-in-oil emulsifier,
- c) at least one non-ionic polyalkylene glycol ether with an HLB value >7,
- d) at least one $C_8$-$C_{16}$-isoparaffin, at least one propellant, and an aerosol dispensing device, which, based on the weight of the total propellant-free water-in-oil emulsion, contains less than 5.0 wt. % cyclomethicones, preferably less than 3.0 wt. % cyclomethicones, particularly preferably less than 1.0 wt. % cyclomethicones and in particular no cyclomethicones.

As an optional component, the water-in-oil emulsions according to the invention preferably contain at least one ester of a $C_6$-$C_{30}$ carboxylic acid. These preferably include 2-ethylhexyl palmitate (e.g. Cegesoft® C 24), hexyldecyl stearate (e.g. Eutanol® G 16), hexyldecyl laurate, isodecyl neopentanoate, isononyl isononanoate, 2-ethylhexyl stearate, isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid 2-butyloctanoate, diisotridecyl acetate, n-butyl stearate, n-hexyl laurate, n-decyl oleate, oleyl oleate, oleyl erucate, erucyl oleate, erucyl erucate, ethylene glycol dioleate and dipalmitate. The use of isopropyl esters of $C_{12}$-$C_{18}$ carboxylic acids, in particular the use of isopropyl myristate, has proved particularly advantageous for emulsion stability and active ingredient release.

The proportion by weight of the at least one $C_6$-$C_{30}$ carboxylic acid ester, preferably $C_{12}$-$C_{18}$ carboxylic acid ester, is in total, based on the total propellant-free water-in-oil emulsion, preferably 0.5-18 wt. %, for preference 1.0-16.0 wt. %, in particular 2.0-14 wt. % and extraordinarily preferably 5-10 wt. %.

The present application preferably provides a cosmetic product, encompassing a water-in-oil emulsion, containing
- a) at least one antiperspirant active ingredient,
- b) at least one water-in-oil emulsifier,
- c) at least one non-ionic polyalkylene glycol ether with an HLB value >7,
- d) at least one $C_8$-$C_{16}$ isoparaffin,
- e) 0.5 to 18 wt. % $C_{12}$-$C_{18}$ carboxylic acid ester, at least one propellant, and an aerosol dispensing device.

In another preferred embodiment, the compositions according to the invention contain at least one water-soluble polyol, selected from the water-soluble polyhydric $C_2$-$C_9$ alkanols with 2-6 hydroxyl groups and water-soluble polyethylene glycols with 3-20 ethylene oxide units, and mixtures thereof. Particularly preferred water-in-oil emulsions according to the invention contain at least one water-soluble polyhydric $C_2$-$C_9$ alkanol with 2-6 hydroxyl groups and/or at least one water-soluble polyethylene glycol with 3-20 ethylene oxide units.

Preferred water-in-oil emulsions according to the invention are characterized in that the water-in-oil emulsion further contains at least one water-soluble polyhydric $C_2$-$C_9$ alkanol with 2-6 hydroxyl groups and/or at least one water-soluble polyethylene glycol with 3-20 ethylene oxide units, selected from 1,2-propylene glycol, 1,3-propylene glycol, 2-methyl-1,3-propanediol, glycerol, 1,2-butylene glycol, 1,3-butylene glycol, 1,4-butylene glycol, pentylene glycols such as 1,2-pentanediol and 1,5-pentanediol, hexanediols such as 1,6-hexanediol, hexanetriols such as 1,2,6-hexanetriol, 1,2-octanediol, 1,8-octanediol, dipropylene glycol, tripropylene glycol, diglycerol, triglycerol, erythritol, sorbitol and mixtures of the aforesaid substances. These substances have a positive effect on the residue behavior, emulsion stability and stable sprayability of the water-in-oil emulsions according to the invention during storage. In this respect, a particularly preferred water-soluble polyhydric $C_2$-$C_9$ alkanol with 2-6 hydroxyl groups is 1,2-propylene glycol.

The proportion by weight of the water-soluble polyhydric $C_2$-$C_9$ alkanol with 2-6 hydroxyl groups and/or of the water-soluble polyethylene glycol with 3-20 ethylene oxide units, based on the total content of these substances in the propellant-free water-in-oil emulsion, is preferably 0.5-35 wt. %, for preference 1.0-30 wt. %, particularly preferably 2-25 wt. %, more preferably 10-20 wt. % or 12-15 wt. %.

Based on the combination of emulsifier, polyalkylene glycol ether and paraffin according to the invention, it is possible to reduce the ethanol content of water-in-oil emulsions according to the invention without impairing the product properties. Preferred water-in-oil emulsions according to the invention therefore contain, based on the total propellant-free water-in-oil emulsion, less than 4.0 wt. % ethanol, preferably less than 3.0 wt. % ethanol and particularly preferably less than 1.0 wt. % ethanol. Most particularly preferred compositions according to the invention are free from ethanol.

The water-in-oil emulsions of the compositions according to the invention contain water preferably in a total quantity of 5-55 wt. %, preferably 10-40 wt. %, particularly preferably 15-30 wt. %, extraordinarily preferably 20-25 wt. %, based in each case on the weight of the total propellant-free water-in-oil emulsion.

The water-in-oil emulsions of the compositions according to the invention preferably contain one or more preservatives. Preferred preservatives according to the invention are formaldehyde donors (such as e.g. 1,3-dimethylol-4,4-dimethylhydantoin, INCI name DMDM Hydantoin), iodopropynyl butylcarbamates such as 3-iodo-2-propynyl butylcarbamate, parabens (i.e. parahydroxybenzoic acid alkyl esters, such as methyl, ethyl, propyl and/or butylparaben), phenoxyethanol, ethanol, benzoic acid, dibromodicyanobutane (2-bromo-2-bromomethylglutarodinitrile), 2-bromo-2-nitropropane-1,3-diol, imidazolidinyl urea, 5-chloro-2-methyl-4-isothiazolin-3-one, 2-chloroacetamide, benzalkonium chloride, benzyl alcohol, salicylic acid and salicylates. Particularly preferred preservatives according to the invention are selected from parabens (methyl, ethyl, propyl and/or butylparaben) and/or phenoxyethanol.

The preservatives are contained in the water-in-oil emulsions according to the invention, based on the total propellant-free water-in-oil emulsion, preferably in a total quantity of 0.01-3, for preference 0.1-1.5 and particularly preferably 0.2-1.0 wt. %.

The composition of some preferred water-in-oil emulsions according to the invention can be taken from the following tables (all data are in wt. %, based on the total weight of the water-in-oil emulsion without propellant):

|  | 1 | 2 | 3 | 4 |
|---|---|---|---|---|
| Antiperspirant active ingredient | 5.0 to 40 | 10 to 40 | 15 to 40 | 20 to 40 |
| Water-in-oil emulsifier | 0.2 to 4.0 | 0.3 to 3.0 | 0.3 to 3.0 | 0.4 to 2.0 |
| Non-ionic polyalkylene glycol ether with an HLB value >7 | 0.1 to 4.0 | 0.2 to 3.0 | 0.2 to 3.0 | 0.2 to 2.0 |
| $C_8$-$C_{16}$ isoparaffin | 4.0 to 20 | 4.0 to 20 | 5.0 to 12 | 6.0 to 10 |

|  | 5 | 6 | 7 | 8 |
|---|---|---|---|---|
| Antiperspirant aluminum salt | 5.0 to 40 | 10 to 40 | 15 to 40 | 20 to 40 |
| Water-in-oil emulsifier | 0.2 to 4.0 | 0.3 to 3.0 | 0.3 to 3.0 | 0.4 to 2.0 |
| Non-ionic polyalkylene glycol ether with an HLB value >7 | 0.1 to 4.0 | 0.2 to 3.0 | 0.2 to 3.0 | 0.2 to 2.0 |
| $C_8$-$C_{16}$ isoparaffin | 4.0 to 20 | 4.0 to 20 | 5.0 to 12 | 6.0 to 10 |

|  | 9 | 10 | 11 | 12 |
|---|---|---|---|---|
| Antiperspirant aluminum salt | 5.0 to 40 | 10 to 40 | 15 to 40 | 20 to 40 |
| PEG/PPG n/m Dimethicone with n + m between 26 and 46 | 0.2 to 4.0 | 0.3 to 3.0 | 0.3 to 3.0 | 0.4 to 2.0 |
| Non-ionic polyalkylene glycol ether with an HLB value >7 | 0.1 to 4.0 | 0.2 to 3.0 | 0.2 to 3.0 | 0.2 to 2.0 |
| $C_8$-$C_{16}$ isoparaffin | 4.0 to 20 | 4.0 to 20 | 5.0 to 12 | 6.0 to 10 |
| Cyclomethicone | <5.0 | <3.0 | <1.0 | — |
| Ethanol | <4.0 | <3.0 | <1.0 | —* |

*in this and the following tables: "—" means "free from"

|  | 13 | 14 | 15 | 16 |
|---|---|---|---|---|
| Antiperspirant aluminum salt | 5.0 to 40 | 10 to 40 | 15 to 40 | 20 to 40 |
| PEG/PPG n/m Dimethicone with n + m between 26 and 46 | 0.2 to 4.0 | 0.3 to 3.0 | 0.3 to 3.0 | 0.4 to 2.0 |
| Non-ionic polyalkylene glycol ether with an HLB value >7 from the group of the alkoxylated $C_8$-$C_{24}$ alkanols with on average 10-100 moles alkylene oxide per mole | 0.1 to 4.0 | 0.2 to 3.0 | 0.2 to 3.0 | 0.2 to 2.0 |
| $C_8$-$C_{16}$ isoparaffin | 4.0 to 20 | 4.0 to 20 | 5.0 to 12 | 6.0 to 10 |
| Cyclomethicone | <5.0 | <3.0 | <1.0 | — |
| Ethanol | <4.0 | <3.0 | <1.0 | —* |

|  | 17 | 18 | 19 | 20 |
|---|---|---|---|---|
| Antiperspirant aluminum salt | 5.0 to 40 | 10 to 40 | 15 to 40 | 20 to 40 |
| PEG/PPG n/m Dimethicone with n + m between 26 and 46 | 0.2 to 4.0 | 0.3 to 3.0 | 0.3 to 3.0 | 0.4 to 2.0 |
| Non-ionic polyalkylene glycol ether with an HLB value >7 | 0.1 to 4.0 | 0.2 to 3.0 | 0.2 to 3.0 | 0.2 to 2.0 |
| $C_{10}$-$C_{13}$ isoalkane | 4.0 to 20 | 4.0 to 20 | 5.0 to 12 | 6.0 to 10 |
| Cyclomethicone | <5.0 | <3.0 | <1.0 | — |
| Ethanol | <4.0 | <3.0 | <1.0 | —* |

|  | 21 | 22 | 23 | 24 |
|---|---|---|---|---|
| Antiperspirant aluminum salt | 5.0 to 40 | 10 to 40 | 15 to 40 | 20 to 40 |
| PEG/PPG n/m dimethicone with n + m between 26 and 46 | 0.2 to 4.0 | 0.3 to 3.0 | 0.3 to 3.0 | 0.4 to 2.0 |
| Non-ionic polyalkylene glycol ether with an HLB value >7 from the group of the alkoxylated $C_8$-$C_{24}$ alkanols with on average 10-100 moles alkylene oxide per mole | 0.1 to 4.0 | 0.2 to 3.0 | 0.2 to 3.0 | 0.2 to 2.0 |
| $C_{10}$-$C_{13}$ isoalkane | 4.0 to 20 | 4.0 to 20 | 5.0 to 12 | 6.0 to 10 |
| Cyclomethicone | <5.0 | <3.0 | <1.0 | — |
| Ethanol | <4.0 | <3.0 | <1.0 | —* |

|  | 25 | 26 | 27 | 28 |
|---|---|---|---|---|
| Antiperspirant aluminum salt | 5.0 to 40 | 10 to 40 | 15 to 40 | 20 to 40 |
| PEG/PPG n/m dimethicone with n + m between 26 and 46 | 0.2 to 4.0 | 0.3 to 3.0 | 0.3 to 3.0 | 0.4 to 2.0 |
| Non-ionic polyalkylene glycol ether with an HLB value >7 from the group of the alkoxylated $C_8$-$C_{24}$ alkanols with on average 10-100 moles alkylene oxide per mole | 0.1 to 4.0 | 0.2 to 3.0 | 0.2 to 3.0 | 0.2 to 2.0 |
| $C_{10}$-$C_{13}$ isoalkane | 4.0 to 20 | 4.0 to 20 | 5.0 to 12 | 6.0 to 10 |
| $C_{12}$-$C_{18}$ carboxylic acid ester | 0.5 to 18 | 1.0 to 16 | 2.0 to 14 | 2.0 to 14 |
| Cyclomethicone | <5.0 | <3.0 | <1.0 | — |
| Ethanol | <4.0 | <3.0 | <1.0 | —* |

|  | 29 | 30 | 31 | 32 |
|---|---|---|---|---|
| Aluminum chlorohydrate | 5.0 to 40 | 10 to 40 | 15 to 40 | 20 to 40 |
| PEG/PPG 18/18 Dimethicone | 0.2 to 4.0 | 0.3 to 3.0 | 0.3 to 3.0 | 0.4 to 2.0 |
| Isoceteth-20 | 0.1 to 4.0 | 0.2 to 3.0 | 0.2 to 3.0 | 0.2 to 2.0 |
| $C_{10}$-$C_{13}$ isoalkane | 4.0 to 20 | 4.0 to 20 | 5.0 to 12 | 6.0 to 10 |
| Isopropyl myristate | 0.5 to 18 | 1.0 to 16 | 2.0 to 14 | 2.0 to 14 |
| Cyclomethicone | <5.0 | <3.0 | <1.0 | — |
| Ethanol | <4.0 | <3.0 | <1.0 | —* |

|  | 33 | 34 | 35 | 36 |
|---|---|---|---|---|
| Antiperspirant active ingredient | 5.0 to 40 | 10 to 40 | 15 to 40 | 20 to 40 |
| Water-in-oil emulsifier | 0.2 to 4.0 | 0.3 to 3.0 | 0.3 to 3.0 | 0.4 to 2.0 |
| Non-ionic polyalkylene glycol ether with an HLB value >7 | 0.1 to 4.0 | 0.2 to 3.0 | 0.2 to 3.0 | 0.2 to 2.0 |
| $C_8$-$C_{16}$ isoparaffin | 4.0 to 20 | 4.0 to 20 | 5.0 to 12 | 6.0 to 10 |
| $C_2$-$C_9$ alkanol with 2-6 hydroxyl groups and/or water-soluble polyethylene glycol with 3-20 ethylene oxide units | 0.5-35 | 1.0-30 | 2-25 | 10-25 |

|  | 37 | 38 | 39 | 40 |
|---|---|---|---|---|
| Antiperspirant aluminum salt | 5.0 to 40 | 10 to 40 | 15 to 40 | 20 to 40 |
| Water-in-oil emulsifier | 0.2 to 4.0 | 0.3 to 3.0 | 0.3 to 3.0 | 0.4 to 2.0 |
| Non-ionic polyalkylene glycol ether with an HLB value >7 | 0.1 to 4.0 | 0.2 to 3.0 | 0.2 to 3.0 | 0.2 to 2.0 |
| $C_8$-$C_{16}$ isoparaffin | 4.0 to 20 | 4.0 to 20 | 5.0 to 12 | 6.0 to 10 |
| $C_2$-$C_9$ alkanol with 2-6 hydroxyl groups and/or water-soluble polyethylene glycol with 3-20 ethylene oxide units | 0.5-35 | 1.0-30 | 2-25 | 10-25 |

|  | 41 | 42 | 43 | 44 |
|---|---|---|---|---|
| Antiperspirant aluminum salt | 5.0 to 40 | 10 to 40 | 15 to 40 | 20 to 40 |
| PEG/PPG n/m Dimethicone with n + m between 26 and 46 (W/O emulsifier) | 0.2 to 4.0 | 0.3 to 3.0 | 0.3 to 3.0 | 0.4 to 2.0 |
| Non-ionic polyalkylene glycol ether with an HLB value >7 | 0.1 to 4.0 | 0.2 to 3.0 | 0.2 to 3.0 | 0.2 to 2.0 |
| $C_8$-$C_{16}$ isoparaffin | 4.0 to 20 | 4.0 to 20 | 5.0 to 12 | 6.0 to 10 |
| Cyclomethicone | <5.0 | <3.0 | <1.0 | — |
| Ethanol | <4.0 | <3.0 | <1.0 | —* |
| $C_2$-$C_9$ alkanol with 2-6 hydroxyl groups and/or water-soluble polyethylene glycol with 3-20 ethylene oxide units | 0.5-35 | 1.0-30 | 2-25 | 10-25 |

*in this and the following tables: "—" means "free from"

|  | 45 | 46 | 47 | 48 |
|---|---|---|---|---|
| Antiperspirant aluminum salt | 5.0 to 40 | 10 to 40 | 15 to 40 | 20 to 40 |
| PEG/PPG n/m Dimethicone with n + m between 26 and 46 (W/O emulsifier) | 0.2 to 4.0 | 0.3 to 3.0 | 0.3 to 3.0 | 0.4 to 2.0 |
| Non-ionic polyalkylene glycol ether with an HLB value >7 from the group of the alkoxylated $C_8$-$C_{24}$ alkanols with on average 10-100 moles alkylene oxide per mole | 0.1 to 4.0 | 0.2 to 3.0 | 0.2 to 3.0 | 0.2 to 2.0 |
| $C_8$-$C_{16}$ isoparaffin | 4.0 to 20 | 4.0 to 20 | 5.0 to 12 | 6.0 to 10 |
| Cyclomethicone | <5.0 | <3.0 | <1.0 | — |
| Ethanol | <4.0 | <3.0 | <1.0 | —* |
| $C_2$-$C_9$ alkanol with 2-6 hydroxyl groups and/or water-soluble polyethylene glycol with 3-20 ethylene oxide units | 0.5-35 | 1.0-30 | 2-25 | 10-25 |

|  | 49 | 50 | 51 | 52 |
|---|---|---|---|---|
| Antiperspirant aluminum salt | 5.0 to 40 | 10 to 40 | 15 to 40 | 20 to 40 |
| PEG/PPG n/m Dimethicone with n + m between 26 and 46 (W/O emulsifier) | 0.2 to 4.0 | 0.3 to 3.0 | 0.3 to 3.0 | 0.4 to 2.0 |
| Non-ionic polyalkylene glycol ether with an HLB value >7 | 0.1 to 4.0 | 0.2 to 3.0 | 0.2 to 3.0 | 0.2 to 2.0 |
| $C_{10}$-$C_{13}$ isoalkane | 4.0 to 20 | 4.0 to 20 | 5.0 to 12 | 6.0 to 10 |
| Cyclomethicone | <5.0 | <3.0 | <1.0 | — |
| Ethanol | <4.0 | <3.0 | <1.0 | —* |
| $C_2$-$C_9$ alkanol with 2-6 hydroxyl groups and/or water-soluble polyethylene glycol with 3-20 ethylene oxide units | 0.5-35 | 1.0-30 | 2-25 | 10-25 |

|  | 53 | 54 | 55 | 56 |
|---|---|---|---|---|
| Antiperspirant aluminum salt | 5.0 to 40 | 10 to 40 | 15 to 40 | 20 to 40 |
| PEG/PPG n/m Dimethicone with n + m between 26 and 46 (W/O emulsifier) | 0.2 to 4.0 | 0.3 to 3.0 | 0.3 to 3.0 | 0.4 to 2.0 |
| Non-ionic polyalkylene glycol ether with an HLB value >7 from the group of the alkoxylated $C_8$-$C_{24}$ alkanols with on average 10-100 moles alkylene | 0.1 to 4.0 | 0.2 to 3.0 | 0.2 to 3.0 | 0.2 to 2.0 |
| $C_{10}$-$C_{13}$ isoalkane | 4.0 to 20 | 4.0 to 20 | 5.0 to 12 | 6.0 to 10 |
| Cyclomethicone | <5.0 | <3.0 | <1.0 | — |
| Ethanol | <4.0 | <3.0 | <1.0 | —* |
| $C_2$-$C_9$ alkanol with 2-6 hydroxyl groups and/or water-soluble polyethylene glycol with 3-20 ethylene | 0.5-35 | 1.0-30 | 2-25 | 10-25 |

|  | 57 | 58 | 59 | 60 |
|---|---|---|---|---|
| Antiperspirant aluminum salt | 5.0 to 40 | 10 to 40 | 15 to 40 | 20 to 40 |
| PEG/PPG n/m Dimethicone with n + m between 26 and 46 (W/O emulsifier) | 0.2 to 4.0 | 0.3 to 3.0 | 0.3 to 3.0 | 0.4 to 2.0 |
| Non-ionic polyalkylene glycol ether with an HLB value >7 from the group of the alkoxylated $C_8$-$C_{24}$ alkanols with on average 10-100 moles alkylene | 0.1 to 4.0 | 0.2 to 3.0 | 0.2 to 3.0 | 0.2 to 2.0 |

-continued

|  | 57 | 58 | 59 | 60 |
|---|---|---|---|---|
| $C_{10}$-$C_{13}$ isoalkane | 4.0 to 20 | 4.0 to 20 | 5.0 to 12 | 6.0 to 10 |
| $C_{12}$-$C_{18}$ carboxylic acid ester | 0.5 to 18 | 1.0 to 16 | 2.0 to 14 | 2.0 to 14 |
| Cyclomethicone | <5.0 | <3.0 | <1.0 | — |
| Ethanol | <4.0 | <3.0 | <1.0 | —* |
| $C_2$-$C_9$ alkanol with 2-6 hydroxyl groups and/or water-soluble polyethylene glycol with 3-20 ethylene | 0.5-35 | 1.0-30 | 2-25 | 10-25 |

|  | 61 | 62 | 63 | 64 |
|---|---|---|---|---|
| Aluminum chlorohydrate | 5.0 to 40 | 10 to 40 | 15 to 40 | 20 to 40 |
| PEG/PPG 18/18 Dimethicone (W/O emulsifier) | 0.2 to 4.0 | 0.3 to 3.0 | 0.3 to 3.0 | 0.4 to 2.0 |
| Isoceteth-20 | 0.1 to 4.0 | 0.2 to 3.0 | 0.2 to 3.0 | 0.2 to 2.0 |
| $C_{10}$-$C_{13}$ isoalkane | 4.0 to 20 | 4.0 to 20 | 5.0 to 1 2 | 6.0 to 10 |
| Isopropyl myristate | 0.5 to 18 | 1.0 to 16 | 2.0 to 14 | 2.0 to 14 |
| Cyclomethicone | <5.0 | <3.0 | <1.0 | — |
| Ethanol | <4.0 | <3.0 | <1.0 | —* |
| 1,2-Propylene glycol | 0.5-35 | 1.0-30 | 2-25 | 10-25 |

In summary, cosmetic products encompassing
a water-in-oil emulsion, containing
a) 5-40 wt. % of an antiperspirant active ingredient from the group of the antiperspirant aluminum salts,
b) 0.2 to 4.0 wt. % water-in-oil emulsifier from the group of the PEG/PPG-n/m Dimethicones with n+m between 26 and 46,
c) 0.1 to 4.0 wt. % of a non-ionic polyalkylene glycol ether with an HLB value >7 from the group of the alkoxylated $C_8$-$C_{24}$ alkanols with on average 10-100 moles alkylene oxide per mole,
d) 4.0 to 20 wt. % of a $C_{10}$-$C_{13}$ isoparaffin mixture,
e) 0.5 to 18 wt. % $C_{12}$-$C_{18}$ carboxylic acid ester,
at least one propellant,
an aerosol dispensing device,
which contain
less than 5.0 wt. % cyclomethicones, preferably less than 3.0 wt. % cyclomethicones, particularly preferably less than 1.0 wt. % cyclomethicones and in particular no cyclomethicones, and
less than 4.0 wt. % ethanol, preferably less than 3.0 wt. % ethanol, particularly preferably less than 1.0 wt. % ethanol and in particular no ethanol,
wherein all of the wt. % data relate to the weight of the propellant-free water-in-oil emulsion, are most particularly preferred.

Cosmetic products encompassing
a water-in-oil emulsion, containing
a) 5-40 wt. % of an antiperspirant active ingredient from the group of the antiperspirant aluminum salts,
b) 0.2 to 4.0 wt. % water-in-oil emulsifier from the group of the PEG/PPG-n/m Dimethicones with n+m between 26 and 46,
c) 0.1 to 4.0 wt. % of a non-ionic polyalkylene glycol ether with an HLB value >7 from the group of the alkoxylated $C_8$-$C_{24}$ alkanols with on average 10-100 moles alkylene oxide per mole,
d) 4.0 to 20 wt. % of a $C_{10}$-$C_{13}$ isoparaffin mixture,
e) 0.5 to 18 wt. % $C_{12}$-$C_{18}$ carboxylic acid ester,
at least one propellant,
an aerosol dispensing device,
which contain
less than 5.0 wt. % cyclomethicones, preferably less than 3.0 wt. % cyclomethicones, particularly preferably less than 1.0 wt. % cyclomethicones and in particular no cyclomethicones, and
less than 4.0 wt. % ethanol, preferably less than 3.0 wt. % ethanol, particularly preferably less than 1.0 wt. % ethanol and in particular no ethanol, and
0.5-35 wt. %, preferably 1.0-30 wt. %, particularly preferably 2-25 wt. % and extraordinarily preferably 10-25 wt. %, of at least one $C_2$-$C_9$ alkanol with 2-6 hydroxyl groups and/or at least one water-soluble polyethylene glycol with 3-20 ethylene oxide units, which is preferably selected from 1,2-propylene glycol,
wherein all of the wt. % data relate to the weight of the propellant-free water-in-oil emulsion, are extraordinarily preferred.

The water-in-oil emulsion according to the invention is contained in an aerosol dispensing device, and the cosmetic product encompasses at least one propellant.

Suitable propellants (propellant gases) according to the invention are propane, propene, n-butane, isobutane, isobutene, n-pentane, pentene, isopentane, isopentene, methane, ethane, dimethyl ether, nitrogen, air, oxygen, laughing gas, 1,1,1,3-tetrafluoroethane, heptafluoro-n-propane, perfluoroethane, monochlorodifluoromethane, 1,1-difluoroethane, either individually or in combination. Hydrophilic propellants, such as e.g. carbon dioxide, can also be used advantageously within the meaning of the present invention if a low proportion of hydrophilic gases is selected and lipophilic propellant (e.g. propane/butane) is present in excess. Particularly preferred are propane, n-butane, isobutane and mixtures of these propellants.

Cosmetic products which contain the propellant in a quantity of 10-90 wt. %, preferably 40-85 wt. % and particularly preferably 50-80 wt. %, based in each case on the total weight of the preparation consisting of the water-in-oil emulsion and the propellant, are preferred according to the invention.

Suitable compressed gas containers are vessels made of metal (aluminum, tin plate, tin), protected or non-shattering plastics or glass with an external coating of plastics, the selection taking into account their pressure resistance and breaking strength, corrosion resistance, ease of filling and aesthetic aspects, handling properties, printability etc. Special internal protective lacquers ensure corrosion resistance with respect to the water-in-oil emulsion.

The deodorizing products according to the invention display particularly high corrosion resistance despite the aqueous phase in the aerosol container, which represents a great advantage over the prior art. Furthermore, the water-in-oil emulsions used according to the invention have excellent skin compatibility, storage stability and effectiveness. It is particularly advantageous that the sprayed products are distinguished by a pleasant, non-sticky feel on the skin. The oil and water content which is balanced according to the invention produces a pleasant fresh feel after application, with high skin compatibility. In a preferred embodiment of the invention the valve has a valve cup coated with a lacquer or a polymeric plastic A and a similar flexible element with return characteristics which resets the valve to the closed position (=rest position of the valve) when actuation is completed. Suitable cosmetic products in which the aerosol dispensing device comprises a valve having a valve cone and/or a flexible element with return characteristics which is/are coated with a lacquer or a polymeric plastic A are preferred according to the invention.

In another preferred embodiment of the invention the valve has a flexible element with return characteristics and/or a valve cup made of at least one plastic B, preferably an elastomeric plastic. Here too, cosmetic products according to the invention in which the valve has a flexible element with return characteristics and/or a valve cone made of at least one plastic B are preferred, preferred plastics B being elastomeric plastics. Particularly preferred elastomeric plastics are selected from Buna, in particular Buna N, Buna 421, Buna 1602 and Buna KA 6712, neoprene, butyl and chlorobutyl.

In another preferred embodiment of the invention, the flexible element with return characteristics can take the form of a coil spring or helical compression spring. In another preferred embodiment of the invention, the flexible element with return characteristics can be designed integrally with the valve cone and can comprise flexible legs. This spring can be made of metal or plastics.

In a particularly preferred embodiment of the invention, the valve cone and flexible element with return characteristics are designed. Particularly preferred in this case is the valve type Ariane M, obtainable from Seaquist Perfect, in which the flexible element with return characteristics is designed integrally with the valve cone in the form of four elastic legs.

All valves used according to the invention preferably have an internally lacquered valve cup, wherein lacquering and valve material are compatible with one another. If aluminum valves are used according to the invention, their valve cups can be coated internally e.g. with Micoflex lacquer. If tin plate valves are used according to the invention, their valve cups can be coated internally e.g. with PET (polyethylene terephthalate). The containers used, which can be made of e.g. tin plate or aluminum, aluminum containers being preferred according to the invention, must also be internally lacquered or coated in view of the corrosiveness of the water-in-oil emulsion used according to the invention. A preferred internal protective lacquer according to the invention is an epoxy-phenol lacquer, as is obtainable e.g. with the name Hoba 7407 P.

As mentioned at the beginning, the agents according to the invention are suitable as cosmetic agents for the treatment of skin and hair. These agents are distinguished by improved active ingredient release and, as a result, by an improved cosmetic action and high skin compatibility. The present application therefore further provides a method for the cosmetic treatment of skin and/or hair, wherein a water-in-oil emulsion containing a) at least one cosmetic active ingredient,
b) at least one water-in-oil emulsifier,
c) at least one non-ionic polyalkylene glycol ether with an HLB value >7,
d) at least one $C_8$-$C_{16}$ isoparaffin, is applied onto the skin and/or hair in the form of an aerosol.

As mentioned at the beginning, the agents according to the invention are suitable as deodorizing agents for the treatment of armpit wetness and body odor. These agents are distinguished by improved active ingredient release and, as a result, by an improved antiperspirant action. The present application therefore further provides a method for the cosmetic treatment of body odor, characterized in that a water-in-oil emulsion, containing a) at least one antiperspirant active ingredient,
b) at least one water-in-oil emulsifier,
c) at least one non-ionic polyalkylene glycol ether with an HLB value >7,
d) at least one $C_8$-$C_{16}$ isoparaffin, is applied onto the skin in the form of an aerosol.

The following examples are intended to explain the subject matter of the invention without limiting it thereto.

The following four water-in-oil emulsions were prepared (data in wt. %) and tested with respect to their emulsion stability and their corrosiveness.

|  | 1(C) | 2(C) | 3(C) | 4(I) | 5(I) |
|---|---|---|---|---|---|
| Aluminum chlorohydrate | 33 | 33 | 33 | 33 | 33 |
| Cyclomethicone | 12 | 9.4 | — | — | — |
| $C_{10}$-$C_{13}$ isoalkane | — | — | 9.4 | 8.9 | 8.9 |
| PEG/PPG-18/18 Dimethicone | — | 1.4 | 1.4 | 1.4 | 1.4 |
| Cetyl PEG/PPG-10/1 Dimethicone | 3.0 | — | — | — | — |
| Isoceteth-20 | — | — | — | 0.50 | 0.50 |
| Dimethicone | 0 | 4.2 | 4.2 | 4.2 | 4.2 |
| Isopropyl myristate | 9.0 | 9.0 | 9.0 | 9.0 | 9.0 |
| 1,2-Propanediol | 7.0 | 7.0 | 7.0 | 7.0 | 25 |
| Phenoxyethanol | 0.50 | 0.50 | 0.50 | 0.50 | 0.50 |
| Perfume | 2.5 | 2.5 | 2.5 | 2.5 | 2.5 |
| Water | to 100 | to 100 | to 100 | to 100 | to 100 |
| Stable emulsion | no | no | no | yes | yes |
| Corrosive | — | — | — | no | no |

Composition 1 which is not according to the invention is based on a combination of cyclomethicone (oil phase) and cetyl PEG/PPG-10/1 dimethicone (water-in-oil emulsifier, used as Abil EM 90 from Evonik), corresponding to the exemplary disclosure of water-in-oil emulsions in the German patent application DE 10 2006 062 499 A1. A combination of this type does not provide a stable emulsion.

Likewise, by exchanging the water-in-oil emulsifier cetyl PEG/PPG-10/1 dimethicone for the water-in-oil emulsifier PEG/PPG-18/18 dimethicone (used as Dow Corning ES-5227 DM) (example 2 which is not according to the invention), no stable emulsion is obtained.

When cyclomethicone is exchanged for $C_{10}$-$C_{13}$ isoalkane, again no stable emulsion can be obtained by using the water-in-oil emulsifier PEG/PPG-18/18 dimethicone (used as Dow Corning ES-5227 DM) (example 3 which is not according to the invention).

Only with a combination of $C_{10}$-$C_{13}$ isoalkane (oil phase) with an emulsifier combination of the water-in-oil emulsifier PEG/PPG-18/18 dimethicone (used as Dow Corning ES-5227 DM) and the oil-in-water emulsifier Isoceteth-20 is the emulsion obtained stable (example 4 according to the invention). The water-in-oil emulsion obtained is non-corrosive after packing in an aluminum can coated with epoxy phenol lacquer in a weight ratio of propellant (butane/propane/isobutane mixture) to emulsion of 80:20.

|  | 5 (I) | 6 (I) |
|---|---|---|
| Aluminum chlorohydrate | 25 | 25 |
| $C_{10}$-$C_{13}$ isoalkane | 8.9 | 8.9 |
| PEG/PPG-18/18 Dimethicone | 1.4 | 1.4 |
| Isoceteth-20 | 0.50 | 0.50 |
| Dimethicone* | 4.2 | 4.2 |
| Isopropyl myristate | 9.0 | 9.0 |
| 1,2-Propanediol | 7.0 | 25 |
| Phenoxyethanol | 0.50 | 0.50 |

-continued

|  | 5 (I) | 6 (I) |
|---|---|---|
| Perfume | 2.5 | 2.5 |
| Water | to 100 | to 100 |
| Stable emulsion | yes | yes |
| Corrosive | no | no |

*ex Dow Corning ES-5227 DM

Emulsion no. 6 according to the invention displayed further improved residue behavior compared with emulsion no. 5 according to the invention, as shown by the test results compiled below:

Emulsion no. 5 left a narrow white circle (scale value 1.1) after the drying time when a standardized quantity was sprayed onto black card, while emulsion no. 6 formed virtually no white residues (scale value 0.1).

In another test setup ("greasy/wet on black"), emulsion no. 5 gave a residue scale value of 0.8 and emulsion no. 6 a residue scale value of 0.6.

Other Formulation Examples According to the Invention

|  | 7 | 8 | 9 |
|---|---|---|---|
| Aluminum chlorohydrate | 25 | 25 | 25 |
| $C_{10}$-$C_{13}$ isoalkane | 7 | 7 | 7 |
| PEG/PPG-18/18 Dimethicone* | 1 | 1 | 1 |
| Isoceteth-20 | 0.30 | 0.30 | 0.30 |
| Dimethicone* | 3 | 3 | 3 |
| 2-Ethylhexyl palmitate | 9.0 | — | — |
| Isopropyl myristate | — | 9.0 | 6.2 |
| Di-(2-ethylhexyl) carbonate | — | — | 2.8 |
| 1,2-Propanediol | 30 | 22 | 22 |
| Phenoxyethanol | 0.50 | 0.50 | 0.50 |
| Perfume | 2.5 | 2.5 | 2.5 |
| Silver lactate | 0.0009 | — | — |
| Menthyl lactate | — | 1.0 | — |
| Water | to 100 | to 100 | to 100 |

*ex Dow Corning ES-5227 DM

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic product, comprising:
   a stable water-in-oil emulsion, comprising
   a) at least one antiperspirant active ingredient,
   b) 0.2-4.0 wt %, based on the total propellant-free water-in-oil emulsion, of at least one water-in-oil emulsifier,
   c) 0.1 to 4.0 wt. %, based on the total propellant-free water-in-oil emulsion, of isoceteth-20,
   d) 4.0-20 wt. %, based on the total propellant-free water-in-oil emulsion, of at least one C8-C16 isoparaffin;
   e) 0.5-35 wt. %, based on the total propellant-free water-in-oil emulsion, of at least one water-soluble polyol selected from the water-soluble polyhydric C2-C9 alkanols with 2-6 hydroxyl groups and a water-soluble polyethylene glycol with 3-20 ethylene oxide units
   at least one propellant; and
   an aerosol dispensing device.

2. The product according to claim 1, wherein the water-in-oil emulsifier b) is selected from the group consisting of the alkoxylated silicone emulsifiers, a substance from the group of the PEG/PPG-n/m dimethicones with n+m>11.

3. The product according to claim 1, wherein the non-ionic polyalkylene glycol ether c) is selected from the group consisting of the alkoxylated C8-C24 alkanols with on average 10-100 moles alkylene oxide per mole.

4. The product according to claim 1, wherein the non-ionic polyalkylene glycol ether c) has an HLB value >9.

5. The product according to claim 1, wherein the isoparaffin d) is selected from the group consisting of isooctane, isononane, isodecane, isoundecane, isododecane, isotridecane, isotetradecane, isopentadecane and isohexadecane, as well as mixtures thereof.

6. The product according to claim 1, wherein the water-in-oil emulsifier b) is selected from PEG/PPG-18/18 dimethicone, which is present as a dispersion in dimethicone having a viscosity of 3-100 cSt at 25° C.

7. The product according to claim 1, wherein the water-in-oil emulsion comprises at least one water-soluble polyethylene glycol selected from the group consisting of 1,2-propylene glycol, 1,3-propylene glycol, 2-methyl-1,3-propanediol, glycerol, 1,2-butylene glycol, 1,3-butylene glycol, 1,4-butylene glycol, 1,2-pentanediol, 1,5-pentanediol, hexanediols, hexanetriols, 1,2-octanediol, 1,8-octanediol, dipropylene glycol, tripropylene glycol, diglycerol, triglycerol, erythritol, sorbitol and mixtures of the aforementioned substances.

8. A method for the cosmetic treatment of skin and/or hair, comprising applying onto the skin and/or hair the cosmetic product according to claim 1.

9. A method for the cosmetic treatment of body odor, comprising applying onto the skin the cosmetic product according to claim 1.

* * * * *